United States Patent [19]

Hussmann et al.

[11] Patent Number: 4,900,865

[45] Date of Patent: Feb. 13, 1990

[54] METHOD FOR PRODUCING A DI-(MONO- OR POLY-)CARBOXYARYL ETHER

[75] Inventors: Gregory P. Hussmann, Batavia; Juergen K. Holzhauer; George E. Kuhlmann, both of Naperville, all of Ill.

[73] Assignee: Amoco Corporation, Chicago, Ill.

[21] Appl. No.: 125,477

[22] Filed: Nov. 25, 1987

[51] Int. Cl.$^4$ .................... C07C 51/16; C07C 51/255
[52] U.S. Cl. .................................... 562/412; 562/416
[58] Field of Search ............................... 562/412, 416

[56] References Cited

FOREIGN PATENT DOCUMENTS 1019573 2/1966 United Kingdom ................ 562/416
2068945 8/1981 United Kingdom ................ 562/416

Primary Examiner—Paul J. Killos
Attorney, Agent, or Firm—James R. Henes; William M. Magidson; Ralph C. Medhurst

[57] ABSTRACT

A method is disclosed for the liquid-phase oxidation of a di- (mono- or poly-)alkylaryl ether in the presence of a catalyst comprising cobalt, manganese and bromine components to a di- (mono- or poly-)carboxyaryl ether.

9 Claims, No Drawings

METHOD FOR PRODUCING A DI-(MONO- OR POLY-)CARBOXYARYL ETHER

BACKGROUND OF THE INVENTION

1. Field of the Invention

This invention relates generally to a method for producing a diaryl ether and more particularly concerns a method for producing a di-(mono-or poly-)carboxyaryl ether by the liquid-phase oxidation of a di-(mono- or poly-)alkylaryl ether in a solvent.

2. Discussion of the Prior Art

Over approximately the past two decades, organic compounds in which two or more carboxylic acid groups are bonded to one or more carboxylic and/or heterocyclic aromatic nuclei have become of increasing interest, either as direct components in or as intermediates for synthetic condensation polymer molecules. Some of the polymers containing repeating units derived from aromatic polycarboxylic acids have found broad spectrum utility in synthetic fibers and films, as well as in various types of resin formulations, whereas others of such polymers have been more limited in scope of application, but are not less useful. The more common nuclei of aromatic polycarboxylic acids that form polymers that are useful for these purposes include certain simple and more complex bridged aromatic ring systems. One important member of the group involving bridged aromatic ring systems can be pictured most simply by the formula: Ar—O—Ar$^1$, where the groups, Ar and Ar$^1$, represent the same or different cyclic aromatic nuclei. In some cases, the aromatic nuclei of such polycarboxylic acids will contain one or more additional ring substituents, such as amino, nitro, halogen, hydroxyl, cyano, sulfonyl, and the like groups. These additional groups do not participate in the principal polymer-forming reactions, but they can be desirable molecular constituents, either because of the properties they impart to the polymer or because they render the initial polymer molecules susceptible to modification by further reaction.

The aromatic polycarboxylic acids used in polymers generally are produced by subjecting aromatic compounds having a plurality of appropriately positioned alkyl substituents on the aromatic ring or rings to oxidation processes. A number of processes have been reported for oxidizing alkylated aromatic compounds using an oxygen-containing gas and a metal-containing catalyst In particular, several prior art patents have disclosed methods for the oxidation of alkylated diaryl ethers. For example, U.S. Pat. No. 2,959,613 discloses a process for the liquid phase oxidation of alkylated compounds of aromatic character or their closely related oxygenated derivatives at 50°–300° C. and at atmospheric or superatmospheric pressure of up to 200 atmospheres, and in the presence of a catalyst having manganese, cobalt and bromine components and additionally in the presence of cations—for example, any basic ions but preferably alkali metals or alkaline earth metals—corresponding to a concentration of from 0.25 to 0.00025 gram atom per gram mole of total organic compounds. Of particular relevance, the patent also discloses that hydrocarbons of aromatic character substituted by at least one alkyl, haloalkyl, or closely related oxygenated derivative of an alkyl or haloalkyl group and by "at least one polar group resistant to oxidation selected from: halogen, —SO$_2$NR'R"(R'R"=alkyl, aryl, or H), —OR(R=alkyl, aryl), —NHCOR(R=alkyl aryl or H), —OCOR(R=alkyl, aryl, or H), —SO$_3$R(R=alkyl, aryl or H), —CONR'R"(R=alkyl, aryl or H), NR'R"(R=alkyl aryl), benzoyl, substituted benzoyl or alkyl carboxylic ester" can also be oxidized to the corresponding carboxylic acids. However, this patent contains no disclosure of a specific, suitable compound containing a polar —OR group where R is an aryl group, that is resistant to oxidation.

U.S. Pat. No. 3,012,038 discloses a process for the liquid-phase oxidation of alkyl or haloalkyl aromatic compounds or heterocyclic compounds of aromatic character or their closely related oxygen-containing derivatives to form carboxylic acids, in the presence of a catalyst having cobalt manganese and bromine components and in a reaction zone which presents surfaces of titanium, tantalum or hafnium. The only ether or sulfide that is disclosed as a starting material is beta, beta'-dichlorodiethylether.

U.S. Pat. No. 3,406,196 discloses a process for the oxidation in two stages of polyalkyl-substituted aromatic compounds to polycarboxylic acids with molecular oxygen in the presence of a catalyst having cobalt, manganese, and bromine components and in the absence of a foreign organic liquid reaction medium. The second oxidation stage is conducted at a temperature that is at least 25° C. higher than the temperature employed in the first oxidation stage. Suitable polyalkylated aromatics include bridged aromatic ring systems pictured most simply by the formula Ar-Ar' and Ar"-X-AR''' where Ar and Ar''' represent like or different cyclic aromatic nuclei and X represents —O—, —SO—, —SO$_2$—, —CO— or —[CRR']—$_n$ where R and R' represent hydrogen and organic radicals and n is a positive integer of at least one. A specific example of a suitable polyalkylated aromatic ether (where X is oxygen) is not disclosed therein.

Tanger, U.S. Pat. Nos. 4,323,692 and 4,401,828 disclose the oxidation of the methyl substituent in

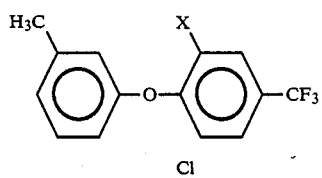

to

wherein R is OR',SR', NR'R' wherein R' is hydrogen, alkyl, substituted alkyl or alkenyl, and wherein X is hydrogen or halogen. The disclosed process employs a cobalt catalyst, a bromide promoter and a hydrogen peroxide activator.

Imamura, U.S. Pat. No. 4,220,605 and the divisional thereof, U.S. Pat. No. 4,272,634, disclose the oxidation at 30–200° C. to an alcohol or aldehyde of the methyl substituent of a toluene derivative of the formula

where R is a hydrocarbyl group with 1-20 carbon atoms which may carry one or more substituents which are described as being inert to the oxidation reaction, and n is an integer of 1 or 2. R may be an aryl group such as phenyl, tolyl, xylyl, ethylphenyl, n-propylphenyl, isopropylphenyl, butylphenyl, naphthyl groups and aralkyl groups such as benzyl and phenethyl groups. The catalyst employed in the oxidation reaction contains a soluble cobalt salt and a bromine ion-supplying substance. Water formed during the reaction is removed from the reaction system. Carboxylic acids are disclosed as by-products whose formation is inhibited under the conditions employed in the claimed method.

Similarly, British Pat. No. 1,546,397 discloses the preparation of formylated phenoxy compounds by the liquid-phase oxidation of methylated phenoxy compounds with an oxygen-containing gas above atmospheric pressure in the presence of a lower fatty acid or anhydride and at least one soluble salt of cobalt, manganese, chromium or nickel.

Back, U.S. Pat. No. 3,453,324 discloses the oxidation of 4,4'-bis(hydroxymethyl)-diphenyl ether to 4,4-bis(carboxy)-diphenylether under essentially anhydrous conditions at a temperature as high as the reflux temperature of the reaction mass and with a specific catalyst system which is described as having as its essential feature that it consists essentially of a cobalt salt of a normally liquid fatty acid and a bromide ion in concentrations which provide at least about one atom of cobalt for every atom of bromine present in the system.

British Pat. No. 951,192 discloses a method for oxidizing aralkyl compounds which may contain oxygen or sulfur, for example, polyalkylaryl ethers and sulfones, such as p,p'-dimethyldiphenyl ether to p,p'-diphenylether dicarboxylic acid, in the presence of a catalyst which comprises cobalt, bromine and a carboxylic acid, which can also be the solvent, and preferably under substantially anhydrous conditions. The catalyst system is described as being so unique and specific that the omission or substitution of one component either totally stops or substantially impedes the reaction.

Similarly, Japanese Kokai-Tokkyo Koho JP 86 63,634 discloses the oxidation of dimethyldiphenyl ethers with molecular oxygen in a lower fatty acid solvent and in the presence of a catalyst containing cobalt and bromine.

One of the difficulties with such prior art oxidation procedures lies in their inability to provide an essentially pure product without expensive and time-consuming separation procedures. Moreover, where polyalkyl derivatives are employed as reactants, the reaction sometimes appears to proceed with the oxidation of one of the alkyl radicals to the exclusion of the remainder. Such byproducts frequently tend to possess solubility properties similar to those possessed by the desired product making separation and purification of the desired product expensive and time-consuming in commercial operations. A further difficulty encountered in such reactions involving the formation of intermediate oxidation products resides in the fact that conditions and catalyst materials which function most efficiently at one stage of the reaction may become less efficient for oxidation at another intermediate stage.

OBJECTS OF THE INVENTION

It is therefore a general object of the present invention to provide an improved process for producing a di-(mono- or poly-)carboxyaryl ether which overcomes the problems of such prior art processes.

Other objects and advantages of the invention will become apparent upon reading the following detailed description and appended claims.

SUMMARY OF THE INVENTION

These objects are achieved by the method of this invention for producing a di-(mono- or poly-)carboxyaryl ether product comprising: oxidizing di-(mono-or poly-)alkylaryl ether reactant with an oxygen-containing gas in the liquid-phase in a solvent in a reactor at a temperature in the range of from about 120° C. to about 240° C. and elevated pressure and in the presence of an oxidation catalyst comprising cobalt, manganese, and bromine components to form a product mixture comprising a di-(mono-or poly-)carboxyaryl ether product, wherein the solvent comprises at least one $C_2$–$C_6$ monocarboxylic acid, and wherein the atom ratio of cobalt (calculated as elemental cobalt) in the cobalt component of the catalyst-to-the ether reactant in the liquid-phase oxidation is in the range of from about 0.1 to about 10 mga per gram mole of the ether reactant, the atom ratio of manganese (calculated as elemental manganese) in the manganese component of the catalyst-to-cobalt (calculated as elemental cobalt) in the cobalt component of the catalyst is in the range of from about 0.1 to about 10 mga per mga of cobalt (calculated as elemental cobalt) and the atom ratio of bromine (calculated as elemental bromine) in the bromine component of the catalyst-to-total cobalt and manganese (calculated as elemental cobalt and elemental manganese) in the cobalt and manganese components of the catalyst is in the range of from about 0.1 to about 5.0 mga per mga of total cobalt and manganese.

DETAILED DESCRIPTION OF THE PREFERRED EMBODIMENTS

The aryl groups in a di-(mono- or poly-)alkylaryl ether that is suitable for use as a reactant in the method of this invention are typically phenyl or naphthyl groups. Typically the alkyl groups to be oxidized in such aryl groups by the method of this invention contain from 1 to 3 carbon atoms and preferably contain 1 carbon atom. Each such alkyl group is located at a position on the aryl group that is not ortho to the ether oxygen and preferably is meta or para to the ether oxygen.

In addition, it is also possible that other groups that are resistant to oxidation in the method of this invention can also be present on the aforesaid aryl groups. Typical such resistant groups include t-butyl, alkoxy, phenyl, naphthyl, phenoxy, naphthoxy, halogen or nitro.

Furthermore, each of the two (mono- or poly-)-alkylaryl groups attached to the ether oxygen in a reactant employed in the method of this invention may be the same as or different from the other (mono- or poly-)alkylaryl group attached to the same oxygen atom. For example, 3,5-dimethylphenyl-3-methylnaphthyl ether and 3,5-dimethylphenyl-3-methylphenyl ether are each suitable as a reactant in the method of this invention. Preferably, the reactant in the method of this invention is 3 (or 4)-alkylphenyl-3 (or 4)-alkylphenyl ether, 3 (or 4)-alkylphenyl-3,4 (or 3,5)-dialkylphenyl ether, 3,4 (or 3,5)-dialkylphenyl-3,4 (or 3,5)-dialkylphenyl ether, 3 or (4,5,6)-alkylnaphthyl-3 (or 4,5,6)-alkylnaphthyl ether, 3 (or 4,5,6)-alkylnaphthyl-3,4 (or 3,5 or 3,6 or 3,7) dialkylnaphthyl ether, 3,4 (or 3,5 or 3,6 or 3,7) dialkylnaphthyl-3,4 (or 3,5 or 3,6 or 3,7) dialkylnaphthyl ether and, more particularly, is 4,4'-dimethyldiphenyl ether, 3,4'-dimethyldiphenyl ether, 3,3'-dimethyldiphenyl ether, or 3,3',4,4'-tetramethyldiphenyl ether.

Suitable solvents for use in the method of this invention include any aliphatic $C_2-C_6$ monocarboxylic acid such as acetic acid, propionic acid, n-butyric acid, isobutyric acid, n-valeric acid, trimethylacetic acid, and caproic acid and mixtures thereof. Since the heat generated in the highly exothermic liquid-phase oxidation is dissipated at least partially by vaporization of the solvent in the oxidation reactor, some of the solvent is withdrawn from the reactor as a vapor, which is then withdrawn from the oxidation reactor as a vent gas, condensed and recycled to the reactor.

Water can be introduced into the reactor from an external source—for example, with fresh or recycled sol- vent—so that such water is present at a level of from about 1 to about 10, preferably from about 4 to about 6, weight percent of the total weight of the acid solvent in the reactor. Water is also formed as a by-product in the oxidation reaction, and if necessary or desired in order to maintain the concentration of water being introduced into the reactor within the aforesaid concentration range therefor before being recycled, water can be separated from the monocarboxylic acid solvent during condensation in order to reduce the concentration of water being introduced to the reactor in the recycle solvent.

The weight ratio of solvent-to-the ether reactant employed in the oxidation is from about 1:1 to about 10:1, and preferably from about 3:1 to about 6:1.

The source of molecular oxygen employed in the oxidation step of the method of this invention can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture containing from 0.5 to 8 volume percent oxygen (measured on a solvent-free basis). For example, a feed rate of the oxygen-containing gas sufficient to provide oxygen in the amount of from 1.5 to 2.8 moles per methyl group or methylene group in the alkyl substituents being oxidized will provide such 0.5 to 8 volume percent of oxygen (measured on a solvent-free basis) in the gas-vapor mixture withdrawn from the reactor. For example, a feed rate of the oxygen-containing gas that is sufficient to provide oxygen in the amount of from 1.5 to 2.8 moles per methyl group will provide such 0.5 to 8 volume percent of oxygen (measured on a solvent-free basis) in the gas-vapor mixture in the condenser.

The catalyst employed in the method of this invention comprises cobalt, manganese, and bromine components, and can additionally comprise accelerators known in the art. Preferably, the catalyst consists essentially of the cobalt-, manganese-, and bromine-containing components. The weight ratio of cobalt (calculated as elemental cobalt) in the cobalt component of the catalyst-to-the ether reactant in the liquid-phase oxidation is in the range of from about 0.1 to about 10 milligram atoms (mga) per gram mole of the ether reactant The weight ratio of manganese (calculated as elemental manganese) in the manganese component of the catalyst-to-cobalt (calculated as elemental cobalt) in the cobalt component of the catalyst in the liquid-phase oxidation is in the range of from about 0.1 to about 10 mga per mga of cobalt. The weight ratio of bromine (calculated as elemental bromine) in the bromine component of the catalyst-to-total cobalt and manganese (calculated as elemental cobalt and elemental manganese) in the cobalt and manganese components of the catalyst in the liquid-phase oxidation is in the range of from about 0.1 to about 5.0 mga per mga of total cobalt and manganese.

Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromide can be employed. The 0.1:1 to 5:1 bromine-to-total cobalt and manganese milligram atom ratio is provided by a suit-able source of bromine. Such bromine sources include molecular bromine ($Br_2$), or ionic bromide (e.g., HBr, NaBr, KBr, $NH_4Br$, etc.), or organic bromides which are known to provide bromide ions at the operating temperature of the oxidation (e.g., bromobenzenes, benzyl bromide, mono- and di-bromoacetic acid, bromoacetyl bromide, tetrabromoethane, ethylene dibromide, etc.). The total bromine in molecular bromine and ionic bromide is used to determine satisfaction of the elemental bromine-to-total cobalt and manganese milligram atom ratio of 0.1:1 to 5:1. The bromide ion released from the organic bromides at the oxidation operating conditions can be readily determined by known analytical means. Tetrabromoethane, for example, at operating temperatures of 170° C. to 225° C. has been found to yield about 3 effective gram atoms of bromine per gram mole.

In operation, the minimum pressure at which the oxidation reactor is maintained is that pressure which will maintain a substantial liquid phase of the ether reactant and at least 70 percent of the solvent. The ether and solvent not in the liquid phase because of vaporization are removed from the oxidation reactor as a vapor-gas mixture, condensed, and then returned to the oxidation reactor. When the solvent is a mixture of acetic acid containing up to 10 weight percent of water, suitable reaction gauge pressures in the oxidation reactor are in the range of from about 0 kg/cm² to about 35 kg/cm², and typically are in the range of from about 10 kg/cm² to about 30 kg/cm2. The temperature range within the oxidation reactor is generally from about 120° C., preferably from about 140° C., to about 240° C., preferably to about 230° C. The solvent residence time in the oxidation reactor is generally from about 20 to about 150 minutes and preferably from about 30 to about 120 minutes.

The oxidation of the method of this invention can be performed either on a batch, continuous or semi-continuous mode. In the batch mode, the aforesaid ether reactant solvent (including water added from an external source) and the cobalt, manganese and bromine components are initially introduced batchwise into the reactor, and the temperature and pressure of the reactor contents are then raised to the desired levels therefor for the commencement of the oxidation reaction. Air is introduced continuously into the reactor. After commencement of the oxidation reaction—for example, after all of the aromatic feed compound had been completely introduced into the reactor—the temperature of the reactor contents is raised. In the continuous mode, each of the ether reactant, air, solvent (including water added from an external source) and the catalyst components dissolved in solvent are continuously introduced through a first inlet or set of inlets into a first oxidation reactor where, in an upstream portion thereof, the temperature and pressure are at the desired levels therefor for initiation of the oxidation reaction; and a product stream comprising the ether product and catalyst components dissolved in the solvent is withdrawn from the reactor. Downstream oxidation reactor(s) containing the effluent from the aforesaid first oxidation reactor or points in the aforesaid first oxidation reactor that are downstream of the aforesaid first inlet(s) are generally operated at higher temperatures or with additional amounts of catalyst or some other enhanced oxidation condition. In the semi-continuous mode, the solvent (including the water added from an external source) and the cobalt, manganese, and bromine components are initially introduced batchwise into the reactor, and then the ether reactant and air are introduced continuously into the reactor. After commencement of the oxidation reaction, the temperature of the reactor contents is raised. Preferably, as is described hereinbelow, the semi-continuous mode is employed for the oxidation of the method of this invention.

In each case, the progress of the reaction is monitored by measuring oxygen uptake and temperature changes. A run is terminated after oxygen uptake ceases, as evidenced by a rapid decrease in oxygen uptake—that is, by a rapid increase in the oxygen concentration in the vapor-gas mixture withdrawn from the reactor.

Thereafter, the product stream in the continuous mode or the reactor contents in the batch or semi-continuous mode are cooled to a temperature in the range of from about 60° C. to about 50° C. in at least one step and in at least one crystallizer such that essentially all of the resulting crude, solid ether product is separated from the product mixture typically by filtration or centrifugation at a temperature in the range of from about 90° C. to about 130° C. The use of lower temperatures results in the recovery of a significantly less pure product and the use of higher temperatures results in the recovery of significantly less product.

Preferably the separated crude ether product can be purified by recrystallization from a recrystallization solvent comprising a $C_2$-$C_6$ monocarboxylic acid such as acetic acid, optionally containing up to 20 weight percent of water, at 80°-316° C. and with a weight ratio of 1-20 parts of the recrystallization solvent per part of the crude ether product. For example, 75 grams of crude 3,3'-dicarboxydiphenyl ether prepared in accordance with the method of this invention were dissolved in a stirred, heated autoclave in 300 9rams of a recrystallization solvent containing 95 weight percent of acetic acid and 5 weight percent of water at 240° C. and held at that temperature for 30 minutes. The solution was then cooled to 82° C. and filtered. The autoclave was rinsed with 75 grams of the recrystallization solvent, and the filter cake was washed with this rinse liquid. After drying this cake at 90° C. and under a vacuum of 20 inches of mercury for 16 hours, 67.7 grams of the resulting dry purified cake were recovered. This purified 3,3'-dicarboxydiphenyl ether had an optical density of 0.505 (measured as described hereinbelow for Examples 19-31), an ash content of 126 weight parts per million, 22 weight parts per million of bromine, 80 parts per million of p-formylphenoxybenzoic acid, 8.4 weight parts per million of cobalt, and 3.93 weight parts per million of manganese. By contrast, the crude 3,3'-dicarboxydiphenyl ether had an optical density of 1.48, and an ash content of 1540 weight parts per million, 120 weight parts per million of bromine, 420 weight parts per million of p-formylphenoxybenzoic acid, 196 weight parts per million of cobalt, and 60 weight parts per million of manganese.

In the alternative, the separated crude ether product is substantially purified by esterifying all of the carboxylic acid groups to form their methyl or ethyl esters and then purifying the esterified ether product either by distillation or by recrystallization of it from a suitable recrystallization solvent such as benzene, toluene, a xylene, an aliphatic hydrocarbon or a halogenated aliphatic hydrocarbon or mixtures thereof.

Suitably the esterification is performed using methanol as both a reactant and the solvent at about 60° C. to about 325° C. for 0.5 to 8 hours with a strong acid—for example, sulfuric acid—or heavg metal—for example, cobalt, manganese or zinc—catalyst at 0-3000 pounds per square inch gauge. Thereafter the reactor is depressurized and the solution is cooled to a temperature where the ether product crystallizes and is then separated by filtration or centrifugation. Typically, 12.9 parts by weight of the crude ether product, 1.25 part by weight of 80% sulfuric acid and 100 parts by weight of methanol are heated for about 5 hours at 120° C. with agitation under a nitrogen atmosphere, at a pressure of about 100 pounds per square inch gauge. (The esterification can also be performed at atmospheric pressure.) Thereafter the esterification reactor is depressurized, and its contents are cooled to about 65° C., the methylated ether product is filtered from the product mixture and is washed with an equal volume of cold methanol. Typically yields of about 95 mole percent of the ester based on the ether product are obtained using this process. In the alternative, a zinc oxide esterification catalyst has been employed at 260-320° C. and 1500-3000 pounds per square inch gauge and a one-hour reaction time.

The resulting wet methylated ether product is heated at 95° C. to 130° C. in benzene, toluene, a xylene, an aliphatic hydrocarbon or a halogenated aliphatic hydrocarbon, or mixtures thereof, such as xylenes or ethylbenzene recrystallization solvent first for about 30 minutes to remove methanol and then to permit treatment with calcium hydroxide and optionally activated carbon. For example, about 65.4 parts of the wet methylated ether product containing about 50 weight percent of methanol is heated in 100 parts by weight of one or more xylenes to distill off the methanol. Thereafter, the mixture is cooled to about 80-90° C. and admixed with 4 parts of water, 2 parts of powdered Nucher S-N or granular Darco 12-20 mesh activated carbon, and 1 part of calcium hydroxide and held at that temperature for about two hours, at which point the mixture is heated to about 120°-140° C. and held there for 6-60 minutes to remove the water as an azeotropic mixture with xylene(s). Thereafter, the solution is cooled to about 20-30° C. to recrystallize the purified methylated ether product, which is separated from the mother liquor by filtration or centrifugation. The resulting separated purified ether is then washed with an equal volume of one or more xylene at room temperature and then dried at about 110° C.

Although this recrystallization procedure, but without the activated carbon, dramatically improves the purity of the ether product, the observed color of the esterified ether product is further improved and a white product is produced if the crude product is subjected to treatment with both a carbon absorbent and calcium hydroxide, during the aforesaid heating in the recrystallization solvent. In such case, while the esterified ether product is dissolved in the recrystallization solvent, the solution is contacted with a carbon absorbent and calcium hydroxide, typically at a level of, for example, about 3 to 6 weight percent of the dissolved ether. For example, 1 part of calcium hydroxide, 2 parts of activated carbon, and about 4 parts of distilled water can suitably be added when the wet product is mixed with one or more xylene and heated. The solid absorbent is separated from the solution by filtering the solution hot, preferably through a filter aid such as Celite 535 or Celite Hyflow Super-Cel, before the purified esterified ether product is crystallized from it. The purified product resulting from this treatment with carbon and calcium hydroxide has a substantially improved (whiter) color as indicated by its optical density or visual appearance.

The present invention will be more clearly understood from the following specific examples.

EXAMPLES 1-18

Each of Examples 1-18 involves the oxidation of an aforesaid ether reactant of the method of this invention on a batch basis and was performed in a one or two liter autoclave equipped with a stirrer, air line, cooling coil, and a line for introduction of air during the oxidation. The temperature of the reactor was controlled by insulated electrical heaters which surrounded the autoclave, and the cooling coil in the reactor. A controlled rate of fluid was passed through the cooling coil during the oxidation. The vented gases from the reactor were passed through a series of condensers, cooled by dry ice, and then through instruments which recorded the gaseous flow rate and the concentration of oxygen and carbon dioxide in the gas stream. Typically, the acetic acid solvent, ether feed and catalyst components containing dissolved therein were added to the autoclave, and the reactor was purged and pressurized to 300-400 pounds per square inch gauge with a slow addition of nitrogen gas. The temperature of the reactor was brought up to the initiation temperature and then the reaction started by stopping the nitrogen gas flow and starting a flow of air through the reactor. The pressure of the reactor was controlled by a research control valve. The rate of oxidation was determined by measuring the oxygen content of the vent gas and knowing the flow rate of air through the reactor and was employed as a measure of the extent of conversion of the ether reactant. The reaction was terminated after oxygen uptake had ceased, whereupon the flow of air into the reactor was replaced by a flow of nitrogen gas into the reactor. Catalyst metal components were introduced in the form of their acetate tetrahydrates, and the bromine component was added as HBr. The specific experimental conditions employed and the results from Examples 1-18 are presented in Table 1. In Examples 1-15, the ether reactant was 4,4'-dimethyldiphenyl ether and was converted to 4,4'-dicarboxydiphenyl ether. In Example 16, 3,4'-dimethyldiphenyl ether was converted to 3,4'-dicarboxydiphenyl ether. In Example 17, 3,3'-dimethyldiphenyl ether was converted to 3,3'-dicarboxydiphenyl ether. In Example 18, 3,3',4,4'-tetramethyldiphenyl ether was converted to 3,3',4,4'-tetracarboxy diphenyl ether. In Examples 5-15, the solvent included 5 weight percent of water added from an external source. In Examples 1-4 and 16-18, no water was added from an external source In Examples 5, 12, 14 and 15, the optical density of 0.5 grams of the cake was measured at 340 nanometers in 30 milliliters of 3 N potassium hydroxide in a 10 millimeter cell. In each of Examples 5, 12, 14 and 15, the optical density measured was greater than 3.

TABLE 1

| Example No. | Catalyst Composition Co[1] | Co:Mn:Br[2] | Acid Solvent:Feed Ratio[3] | Reaction Temperature[4] | Cake Yield[5] |
|---|---|---|---|---|---|
| 1 | 0.18 | 1:1:1.7 | 5:1 | 143 | 91 |
| 2 | 0.40 | 1:0:0.8 | 5:1 | 148 | 91 |
| 3 | 0.12 | 1:1:2.6 | 5:1 | 147 | 90 |
| 4 | 0.12 | 1:0:2.6 | 5:1 | 149 | 83 |
| 5 | 0.12 | 1:0:2.6 | 10:1 | 149 | 72 |
| 6 | 0[6] | 0:1:2.6 | 10:1 | 149 | 0 |
| 7 | 0[7] | 0:1:0.7 | 10:1 | 149 | 0 |
| 8 | 0.12 | 1:0:0 | 10:1 | 149 | 0 |
| 9 | 0.12 | 1:1:0 | 10:1 | 149 | 0 |
| 10 | 0.12 | 1:0:2.6 | 10:1 | 149 | 0 |
| 11 | 0.12 | 1:0:2.6 | 10:1 | 149 | 0 |
| 12 | 0.40 | 1:0:0.8 | 10:1 | 149 | 107[8] |
| 13 | 0.12 | 1:1:2.6 | 10:1 | 149 | 0 |
| 14 | 0.12 | 1:1:2.6 | 10:1 | 149 | 111[8] |
| 15 | 0.12 | 1:1:2.6 | 10:1 | 149 | 107[8] |
| 16 | 0.005 | | 5:1 | 149 | 81 |
| 17 | 0.005 | | 5:1 | 149 | 80 |
| 18 | 0.018 | | 5:1 | 163 | 70 |

[1]Weight percent of acid solvent
[2]Atomic ratio
[3]By weight
[4]°C.
[5]Mole percent of ether feed
[6]With a manganese concentration of 0.12 weight percent of acid solvent
[7]With a manganese concentration of 0.40 weight percent of acid solvent
[8]Weight percent of ether feed Comparison of the results for Examples 1-4 illustrates that, even when water is not added from an external source, the presence of a manganese component in the catalyst is essential in order to afford high yield of the desired product without the necessity of employing relatively larger concentrations of the cobalt component.

Comparison of the results for Examples 10, 11 and 12 illustrates that, when water is added from an external source, and a manganese component is not employed, the oxidation reaction of the method of this invention does not proceed at all unless a relatively high concentration of the cobalt component is employed. By contrast, comparison of the results of Examples 10, 11, 14 and 15 illustrates that, when water is added from an external source and a manganese component is employed, a relatively substantially lower concentration of the cobalt component can be used to afford suitable yields.

Comparison of the results of Examples 13 and 14 illustrates the criticality of the reaction temperature in the method of this invention. The results of Examples 6-9 illustrate the criticality of the bromine and cobalt components.

EXAMPLES 19-31

Each of Examples 19-31 involves the oxidation of 4,4'-dimethyldiphenylether on a semi-continuous basis. In these examples, an acetic acid solvent (including water added from an external source at a concentration of 3 weight percent based on the acetic acid) and the cobalt, manganese (added in the form of their acetate tetrahydrates), and bromine (added as HBr) components of the catalyst were introduced batchwise into either a one-liter reactor (Examples 19-25) or a five-gallon reactor (Examples 26-31), each equipped essentially the same as the reactor employed in Examples 1-18. The temperature and pressure of the reactor contents were raised to the desired levels therefor for the oxidation, and then 4,4'-dimethyldiphenylether at a rate of 1-20 grams per minute and air were introduced continuously into the reactor. Introduction of all of the 4,4'-dimethyldiphenylether required 50-81 minutes in each of Examples 19-31.

The conditions employed in and results from Examples 19-31 are presented in Tables 2 and 3, respectively.

TABLE 2

| Example No. | Catalyst Composition Co[1] | Co:Mn:Br[2] | Total Acid Solvent:Feed Ratio[3] | Reaction Temperature[4] | Reaction Time[5] |
|---|---|---|---|---|---|
| 19 | 0.12 | 1:3:0.9 | 5.1:1 | 160 | 50 |
| 20 | 0.12 | 1:1:2.7 | 3.4:1 | 160 | 75 |
| 21 | 0.24 | 1:1:2.7 | 5.1:1 | 160 | 50 |
| 22 | 0.24 | 1:1:2.7 | 5.1:1 | 193-204 | 50 |
| 23 | 0.24 | 1:1:0.9 | 5.1:1 | 160 | 50 |
| 24 | 0.24 | 1:0:0.5 | 5.1:1 | 160 | 50 |
| 25 | 0.24 | 3:1:2 | 3.4:1 | 193 | 75 |
| 26 | 0.30 | 3:1:2.1 | 3.5:1 | 193 | 81 |
| 27 | 0.30 | 3:1:2.1 | 3.5:1 | 193 | 71.5 |
| 28 | 0.30 | 3:1:2.1 | 3.5:1 | 193 | 71.5 |
| 29 | 0.30 | 3:1:2.1 | 3.5:1 | 193 | 76 |
| 30 | 0.30 | 3:1:2.1 | 3.5:1 | 193 | 76 |
| 31 | 0.30 | 3:1:2.1 | 3.5:1 | 193 | 74 |

[1]Weight percent of acid solvent
[2]Atomic ratio
[3]By weight
[4]°C.
[5]Minutes

TABLE 3

| Ex. No. | Yield Product[1] | Carbon[2] Oxides | Product Optical Quality[3] | Product Impurities Content[4] Co | Mn | Br |
|---|---|---|---|---|---|---|
| 19 | 123 | 2.3 | 1.0 | 45 | 130 | 18 |
| 20 | 162[5] | 3.0 | — | 108 | 117 | 410 |
| 21 | 138[5] | 2.9 | 1.14 | 88 | 93 | 490 |
| 22 | 127 | 2.8 | >5 | 203 | 210 | 1690 |
| 23 | 128 | 2.2 | — | 92 | 97 | 197 |
| 24 | 137[5] | 3.6 | 0.93 | 100 | <2 | 154 |
| 25 | 131[5] | 6.5[6] | 1.43 | 490 | 440 | 123 |
| 26 | 122 | 5.3[6] | 1.57 | 160 | 43 | 94 |
| 27 | 112 | 4.9[6] | 1.87 | 170 | 47 | 97 |
| 28 | 112 | 5.2[6] | 1.93 | 365 | 104 | 134 |
| 29 | 114 | 5.0[6] | 1.51 | 205 | 58 | 130 |
| 30 | 113 | 5.3[6] | 1.44 | 244 | 71 | 123 |
| 31 | 117 | 4.9[6] | 1.48 | 254 | 72 | 114 |

[1]Yield in wt % of feed. Theoretical is 130 wt %.
[2]Mole percent of feed.
[3]Optical density of 0.5 grams of the initial cake ether measured at 340 nanometers in 30 milliliters of 3N potassium hydroxide in a 10 millimiter cell.
[4]Parts per million based on the weight of the total cake.
[5]The products contained some potassium that was used to wash the product from the reactor.
[6]Calculated as if one-half of measured carbon oxides were derived from feed.

Comparison of the results of Examples 1-18 with the results of Examples 19-31 illustrates that performance of the method of this invention in the semi-continuous mode rather than in the batch mode affords a substantially purer product having a substantially lower optical density. Hence, it is highly preferred to practice the method of this invention in a semi-continuous mode.

EXAMPLES 32-34

In each of Examples 32-34, 4,4'-dimethyloxybisbenzoate, that was prepared by esterification of 4,4'-dicarboxydiphenyl ether with methanol in accordance with the method of this invention and that was wet with excess methanol was heated with calcium hydroxide (and additionally in Examples 33 and 34 with a granular Darco 12/20 mesh carbon adsorbent) in m-xylene at 120° C. for 30 minutes to remove the unreacted methanol. Thereafter, the solution in m-xylene was cooled to 85° C., water was added to the solution and the temperature of the resulting mixture was held at 85° C. for 2 hours, and then raised to 95-100° C. for about 30 minutes to remove the water.

In Examples 33 and 34 the resulting mixture was additionally filtered through Celete 535 filter 'aid. Thereafter, in each of Examples 32-34, the solution was cooled to 25° C. to recrystallize the purified methylated ether product, which was then separated from the mother liquor by filtration and finally washed with an equal volume of m-xylene at room temperature and dried at 110° C.

The amounts and conditions employed but not mentioned above are listed in Table 4. The characteristics of the purified methylated ether product are also listed in Table 4.

From the above description, it is apparent that the objects of the present invention have been achieved. While only certain embodiments have been set forth, alternative embodiments and various modifications will be apparent from the above description to those skilled in the art. These alternatives and modifications are considered equivalents and within the spirit and scope of the present invention.

TABLE 4

|  | Example 32 | Example 33 | Example 34 |
|---|---|---|---|
| Wt. of wet 4,4'-dimethyloxybisbenzoate, g | 60 | 60 | 180 |
| Methanol content of 4,4'-dimethyloxybisbenzoate, wt. % | 57 | 57 | 45 |
| Wt. of m-xylene recrystallization solvent, g | 100 | 100 | 275 |
| Wt. of calcium hydroxide, g | 1.0 | 1.0 | 3.0 |
| Wt. of carbon adsorbent, g[1] | 0.0 | 2.0 | 6.0 |
| Wt. of water added, g | 4.0 | 4.0 | 12.0 |
| Recovery of dry 4,4'-dimethyloxybisbenzoate, wt. % of wet 4,4'-dimethyloxybisbenzoate | 70 | 70 | 68 |
| Characteristics of dry 4,4'-dimethyloxybisbenzoate |  |  |  |
| Melting pt., °C. (L:T. Value 153 | 153-154 | 153-154 | 153-154 |
| Haze, N.T.U. | 2.65 | — | 0.55 |
| YIE Value −154 °C.) | 0.40 | — | 0.07 |
| Ash, ppm[1] | 82,142 | — | 219 |
| Aged Molten Color at 340° F. APHA |  |  |  |
| Initial | >100 | 75 | — |
| 4 Hours | >100 | 75 | — |

[1]Granular Darco 12/20 mesh carbon has 17.4 wt. % ash content, some of which may be leached out during product purification.

Having described the invention, what is claimed is:
 1. A method for producing a di-(mono- or poly-) carboxyaryl ether product comprising: oxidizing a di- (mono- or poly-)alkylaryl ether reactant with an oxygen-containing gas in the liquid-phase in a solvent in a reactor at temperatures in the range of from about 120° C. to about 240° C. and elevated pressure and in the presence of an oxidation catalyst comprising cobalt, manganese, and bromine components to form a product mixture comprising a di-(mono- or poly-)carboxyaryl ether product, wherein the solvent is at least one $C_2$–$C_6$ mono-carboxylic acid, and wherein the weight ratio of cobalt (calculated as elemental cobalt) in the cobalt component of the catalyst-to-the ether reactant in the liquid-phase oxidation is in the range of from about 0.1 to about 10 mga per gram mole of the ether reactant, the weight ratio of manganese (calculated as elemental manganese) in the manganese component of the catalyst-to-cobalt (calculated as elemental cobalt) in the cobalt component of the catalyst is in the range of from about 0.1 to about 10 mga per mga of cobalt (calculated as elemental cobalt) and the weight ratio of bromine (calculated as elemental bromine) in the bromine component of the catalyst-to-total cobalt and manganese (calculated as elemental cobalt and elemental manganese) in the cobalt and manganese components of the catalyst is in the range of from about 0.1 to about 5.0 mga per mga of total cobalt and manganese, wherein the ether product is purified either by:

(a) recrystallization of the ether product from a recrystallization solvent comprising a $C_2$–$C_6$ monocarboxylic acid, or (b) esterifying with methanol or ethanol at 60–325° C. and 0–3000 pounds per square inch gauge to form a crude esterified ether solid product, separating the crude esterified ether product, and dissolving the crude esterified ether product in a recrystallization solvent comprising benzene, toluene, a xylene, an aliphatic hydrocarbon, or a halogenated aliphatic hydrocarbon or a mixture, and containing calcium hydroxide, crystallizing the resulting purified esterified ether product from the recrystallization solvent.

2. The method of claim 1 wherein the weight ratio of solvent-to-the ether reactant in the oxidation reactor is from about 1:1 to about 10:1.

3. The method of claim 1 wherein water from an external source is introduced into the reactor such that such water is present at a level of from about 1 to about 10 weight percent of the total weight of acid solvent in the reactor.

4. The method of claim 1 wherein the oxidation step is performed at a temperature in the range of from about 140° C. to about 230° C.

5. The method of claim 1 wherein the atom ratio of cobalt (calculated as elemental cobalt) in the cobalt component of the catalyst-to-the ether reactant in the liquid-phase oxidation is in the range of from about 0.1 to about 10 mga per gram mole of the ether reactant, the atom ratio of manganese (calculated as elemental manganese) in the manganese component of the catalyst-to-cobalt (calculated as elemental cobalt) in the cobalt component of the catalyst is in the range of from about 0.1 to about 10 mga per mga of cobalt, and the atom ratio of bromine (calculated as elemental bromine) in the bromine component of the catalyst-to-total cobalt and manganese (calculated as elemental cobalt and elemental manganese) in the cobalt and manganese components of the catalyst is in the range of from about 0.1 to about 5.0 mga per mga of total cobalt and manganese.

6. The method of claim 1 wherein the solvent residence time in the oxidation reactor is from about 20 to about 150 minutes.

7. The method of claim 1 wherein the oxidation is performed semi-continuously.

8. The method of claim 1 wherein the ether reactant is 3,3'-dimethyldiphenyl ether, 3,4'-dimethyldiphenyl ether, 4,4'-dimethyldiphenyl ether, or 3,3',4,4'-tetramethyldiphenyl ether.

9. The process of claim 1 wherein the ether product is purified by esterifying with methanol or ethanol at 60–325° C. and 0–3000 pounds per square inch gauge to form a crude esterified ether solid product, separating the crude esterified ether product, and dissolving the crude esterified ether product in a recrystallization solvent comprising benzene, toluene, a xylene, an aliphatic hydrocarbon, or a halogenated aliphatic hydrocarbon or a mixture, and containing calcium hydroxide, crystallizing the resulting purified esterified ether product from the recrystallization solvent.

* * * * *